United States Patent

Angenendt et al.

[11] Patent Number: 5,446,201
[45] Date of Patent: Aug. 29, 1995

[54] DI(3-(2-CHLOROETHYLSULFONYL)-1-PROPYL-)AMINE HYDROCHLORIDE AND A PROCESS FOR ITS PREPARATION

[75] Inventors: Heinrich Angenendt; Michael Meier; Wolfram Schams, all of Frankfurt am Main, Germany

[73] Assignee: Hoechst AG, Frankfurt, Germany

[21] Appl. No.: 159,442

[22] Filed: Nov. 30, 1993

[30] Foreign Application Priority Data

Dec. 2, 1992 [DE] Germany .......... 42 40 421.5

[51] Int. Cl.$^6$ .................................... C07C 321/14
[52] U.S. Cl. ..................... 564/500; 564/224
[58] Field of Search .......... 564/224, 500, 488, 496

[56] References Cited

U.S. PATENT DOCUMENTS

| | | | |
|---|---|---|---|
| 2,824,887 | 2/1958 | Klobbing | 260/454 |
| 3,682,965 | 8/1972 | Hickner et al. | 260/326.84 |
| 4,912,244 | 3/1990 | Tzikas | 564/500 |
| 5,227,527 | 7/1993 | Angenendt et al. | 564/500 |
| 5,278,341 | 1/1994 | Meier et al. | 564/500 |

FOREIGN PATENT DOCUMENTS

| | | |
|---|---|---|
| 0070808 | 1/1983 | European Pat. Off. |
| 518321 | 12/1991 | European Pat. Off. |
| 2040620 | 2/1972 | Germany . |
| 9113867 | 2/1991 | WIPO . |

OTHER PUBLICATIONS

Bulletin of the Academy of Sciences of the USSR, Division of Chemical Science, Bd. 25, Nr. 4, Oct. 1976, New York.

*Primary Examiner*—Shailendra Kumar
*Attorney, Agent, or Firm*—Connolly & Hutz

[57] ABSTRACT

Process for preparing di(3-(2-chloroethylsulfonyl)-1-propyl)amine hydrochloride, by
reacting 1 mol of an N,N-diallylcarboxamide of the formula (1)

$$R\text{-}CON(CH_2\text{--}CH\text{=}CH_2)_2 \qquad (1)$$

in which R is hydrogen, alkyl($C_1$–$C_6$) or cycloalkyl($C_4$–$C_8$) with about 4 to about 8 mol of mercaptoethanol at temperatures of about 0° to about −70° C. in the presence of pure oxygen or a mixture of oxygen with an inert gas or an inert gas mixture, if appropriate in an inert organic solvent, to give the carboxamide of the formula (2)

$$R\text{—}CON(CH_2\text{—}CH_2\text{—}CH_2\text{—}S\text{—}CH_2\text{—}CH_2\text{—}OH)_2 \qquad (2)$$

in which R has the abovementioned meaning,
hydrolyzing this compound with the aqueous solution of an alkaline agent at temperatures of about 40° to about 120° C. at a pH of about 10 to about 14, and
reacting 1 mol of the di(3-(2-hydroxyethylthio)-1-propyl)amine thus obtained with about 4 to about 6 mol of chlorine gas in about 2 to about 15% hydrochloric acid at temperatures of about 20° to about 110° C. to give di(3-(2-chloroethylsulfonyl)-1-propyl)amine hydrochloride.

13 Claims, No Drawings

DI(3-(2-CHLOROETHYLSULFONYL)-1-PROPYL)AMINE HYDROCHLORIDE AND A PROCESS FOR ITS PREPARATION

The invention relates to the novel di(3-(2-chloroethylsulfonyl)-1-propyl)amine hydrochloride and to a three-step process for its preparation via the likewise novel compounds N,N-di(3-(2-hydroxyethylthio)-1-propyl)carboxamide and di(3-(2-hydroxyethylthio)-1-propyl)amine, starting from diallylcarboxamides.

Di(3-(2-chloroethylsulfonyl)-1-propyl)amine hydrochloride is a new useful intermediate for reactive dyes; the N,N-di(3-(2-hydroxyethylthio)-1-propyl)carboxamides and the di(3-(2-hydroxyethylthio)-1-propyl)amine are the precursors of said hydrochloride.

Accordingly, the invention provides a process for preparing di(3-(2-chloroethylsulfonyl)-1-propyl)amine hydrochloride, which has the formula

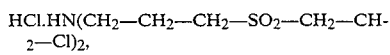

by a) reacting 1 mol of an N,N-diallylcarboxamide of the formula (1)

   (1)

in which R is hydrogen, alkyl($C_1$–$C_6$) or cycloalkyl($C_4$–$C_8$) with at least 2 mol, advantageously with about 4 to about 8 mol, preferably with about 5 to about 7 mol, of mercaptoethanol at temperatures of about 0° to about −70° C. preferably of about −40° to about −60° C., in the presence of pure oxygen or a mixture of oxygen with an inert gas or an inert gas mixture, preferably in the presence of air, if appropriate in an organic solvent which is inert to the reactants and the reaction conditions, at atmospheric pressure or superatmospheric pressure to give the corresponding carboxamide of the formula (2)

R—CON(CH$_2$—CH$_2$—CH$_2$—S—CH$_2$—CH$_2$—OH)$_2$   (2)

in which R has the abovementioned meaning, b) hydrolyzing the carboxamide thus obtained with the aqueous solution of an alkaline agent at temperatures of about 40° to about 120° C. at a pH of about 10 to about 14 to give di(3(2-hydroxyethylthio)-1-propyl)amine, and c) reacting 1 mol of this amine with about 4 to about 6 mol, preferably about 4.1 to about 4.5 mol, of chlorine gas in about 2 to about 15%, preferably about 3 to about 10%, aqueous hydrochloric acid at temperatures of about 20° to about 110° C., preferably about 40° C. to about 80° C., to give di(3(2-chloroethylsulfonyl)-1-propyl)amine hydrochloride.

With regard to the three process steps, the details are as follows:

The procedure of step 1, the reaction of the N,N-diallylcarboxamide with mercaptoethanol, can be such that the two reactants are mixed, the reaction mixture is brought to the reaction temperature and then contacted with the oxygen or with the oxygen-containing mixture, or it can be such that one of the two reactants is introduced first at the reaction temperature and the second reactant is metered in in the presence of oxygen or the oxygen-containing mixture.

In order to avoid side reactions, it is advantageous for the mercaptoethanol to be introduced first at the reaction temperature and for the diallylamide to be metered in in the presence of oxygen or the oxygen-containing mixture.

Examples of inert gases which may be used individually or in a mixture with oxygen are nitrogen and helium.

The reaction can be carried out at atmospheric pressure or superatmospheric pressure. Furthermore, the reaction can take place in an inert organic solvent, such as, for example, toluene or ethanol; however, no advantages can be achieved by this.

Although it is possible to carry out the reaction above 0° C., this increasingly results in side reactions.

After the end of the reaction, excess mercaptoethanol and any by-products formed are distilled off.

Hydrolysis of the compound of the above formula (2) formed in step 1, which is to be carried out in step 2, is advantageously effected using the aqueous solution of an alkali metal hydroxide or alkaline earth metal hydroxide or alkali metal carbonate or alkaline earth metal carbonate, preferably using the aqueous sodium hydroxide solution or potassium hydroxide solution, at the abovementioned temperatures and pH values.

The procedure in step 3, the reaction of the di(3-(2-hydroxyethylthio)-1-propyl)amine obtained in step 2 with chlorine gas, is advantageously such that 1 mol of di(3-(2-hydroxyethylthio)-1-propyl)amine is dissolved in water, the resulting solution is neutralized with about 20 to about 37% aqueous hydrochloric acid, the molar amounts of chlorine mentioned are introduced into the solution at the abovementioned temperatures, and, after cooling the solution, the di(3-(2-chloroethylsulfonyl)-1-propyl)amine hydrochloride is filtered off with suction.

Reaction of di(3-(2-chloroethylsulfonyl)-1-propyl)amine hydrochloride in a known manner with the condensation product obtained by reaction of cyanuric fluoride with 3,6,8.-trisulfonaphthalene-2-azo-(4'-aminobenzene) gives the dye of the formula

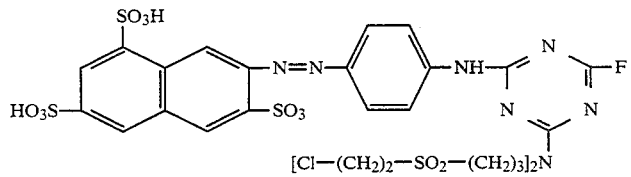

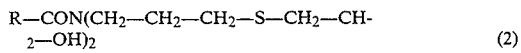

The examples which follow serve to illustrate the process according to the invention without limiting it thereto.

EXAMPLE 1

(reaction step 1)

125.2 g (1.0 mol) of N,N-diallylformamide are metered into 468.8 g (6.0 mol) of mercaptoethanol at −50° C. over a period of 2.5 hours with vigorous stirring while passing air through the reaction mixture. Stirring is subsequently continued until the reaction is complete, and the reaction mixture is then worked up by distillation to give 251.1 g of N,N-di(3-(2-hydroxyethylthio)-1-propyl)formamide, which corresponds to a yield of 90% of theory.

¹H NMR ([D₆]DMSO): δ=1.70, 1.74 (2m; 4H, CH₂—CH₂—CH₂), 2.47, 2.48 (2t, J=7 Hz; 4H, S—CH₂—CH₂—OH), 2.56 (t,J=7 Hz; 4H, S—CH₂), 3.26, 3.30 (2m; 4H, N—CH₂), 3.52 (t,J=7 Hz;4H, CH₂—OH), 4.69 (s; 2H, OH), 8.00 (s; 1H, HCO).

EXAMPLE 2

(reaction step 1)

139.2 g (1.0 mol) of N,N-diallylacetamide are metered into 468.8 g (6.0 mol) of mercaptoethanol at 0° C. over a period of 2 hours with vigorous stirring while passing air through the reaction mixture. Stirring is subsequently continued until the reaction is complete, and the reaction mixture is then worked up by distillation to give 209.8 g of N,N-di(3-(2-hydroxyethylthio)-1-propyl)acetamide, which corresponds to a yield of 71% of theory.

¹H NMR (CDCl₃): δ=1.85, 1.88 (2m; 4H, CH₂—CH₂—CH₂), 2.11 (2; 3H, COCH₃), 2.30 (s; broad; 2H, OH), 2.55, 2.57 (2t, J—7 Hz; 4H, S—CH₂—CH₂—OH), 2.73, 2.75 (2t, J=6 Hz, 4H, S—CH₂), 3.38, 3.43 (2m; 4H, N—CH₂), 3.73, 3.76 (2t, J=6 Hz; 4H, CH₂—OH).

EXAMPLE 3

(reaction step 1)

139.2 g (1.0 mol) of N,N-diallylacetamide are metered into 468.8 g (6.0 mol) of mercaptoethanol at −50° C. over a period of 15 minutes with vigorous stirring while passing air through the reaction mixture. Stirring is subsequently continued until the reaction is complete and the reaction mixture is then worked up by distillation to give 271.8 g of N,N-di(3-(2-hydroxyethylthio)-1-propyl)acetamide, which corresponds to a yield of 92% of theory. The spectroscopic data are identical to those given in Example 2.

EXAMPLE 4

(reaction step 2)

140.7 g of N,N-di(3-(2-hydroxyethylthio)-1-propyl)-formamide (0.5 mol) are refluxed in 160 ml of 20% sodium hydroxide solution until deacylation is complete. This gives 121.5 g of di(3-(2-hydroxyethylthio)-1-propyl)amine, which corresponds to a yield of 96% of theory.

¹H NMR ([D₆]DMSO): δ=1.66 (m; 4H, CH₂—CH₂—CH₂), 2.57, (m; 12H, NCH₂, CH₂SO₂CH₂), 3.58 (t, J=7 Hz; 4H, CH₂OH), 4.02 (s, broad; 3H, OH, NH)

EXAMPLE 5

(reaction step 2)

147.8 g of N,N-di(3-(2-hydroxyethylthio)-1-propyl)acetamide (0.5 mol) are refluxed in 160 ml of 20% sodium hydroxide solution until deacylation is complete. This gives 119.4 g of di(3-(2-hydroxyethylthio)-1-propyl)amine, which corresponds to a yield of 94% of theory. The spectroscopic data are identical to those given in Example 4.

EXAMPLE 6

(reaction step 3)

126.7 g of di(3-(2-hydroxyethylthio)-1-propyl)amine (0.5 mol) are dissolved in 500 ml of water, and 50 ml of 37% hydrochloric acid are added. A total of 155 g of chlorine is then introduced at 80° C. with vigorous stirring until the reaction is finished. After cooling to 0° C., the reaction mixture is filtered off with suction to give, after drying in vacuo, 148.8 g of di(3-(2-chloroethylsulfonyl)1-propyl)amine hydrochloride as colorless crystals of melting point 183°-185° C., which corresponds to a yield of 76% of theory.

¹H NMR ([D₆]DMSO) δ=2.11 (m; 4H, CH₂CH₂CH₂), 3.03 (t, J=6 Hz; 4H, NCH₂), 3.38 (t, J=6 Hz; 4H, NCH₂CH₂SO₂), 3.95 (t, J=6 Hz; 4H, CH₂—Cl), 9.26 (s; 2H, NH₂⁺Cl⁻).

We claim:

1. A process for preparing di(3-(2-chloroethylsulfonyl)-1-propyl)amine hydrochloride, which comprises
   a) reacting each mol of an N,N-diallylcarboxamide of the formula (1)

R—CON(CH₂—CH=CH₂)₂  (1)

in which R is hydrogen, alkyl(C₁-C₆) or cycloalkyl(C₄-C₈) with about 4 to about 8 mol of mercaptoethanol at temperatures of about 0° to about −70° C. in the presence of an oxygen-containing gas optionally in an organic solvent which is inert to the reactants and the reaction conditions, at atmospheric pressure or superatmospheric pressure to give the carboxamide of the formula (2)

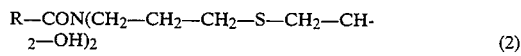

R—CON(CH₂—CH₂—CH₂—S—CH₂—CH₂—OH)₂  (2)

in which R has the abovementioned meaning,
   b) hydrolyzing this carboxamide with an aqueous solution of an alkaline agent at a temperature of about 40° to about 120° C. at a pH of about 10 to about 14, and
   c) reacting each mol of the di(3-(2-hydroxyethylthio)-1-propyl)amine thus obtained with about 4 to about 6 mol of chlorine gas in about 2 to about 15% hydrochloric acid at a temperature of about 20° to about 110° C. to give di(3-(2-chloroethylsulfonyl)-1-propyl)amine hydrochloride.

2. The process as claimed in claim 1, wherein each mol of the N,N-diallylcarboxamide of the formula (1) is reacted with about 5 to about 7 mol of mercaptoethanol.

3. The process as claimed in claim 1, wherein the N,N-diallylcarboxamide is reacted with mercaptoethanol at temperatures of about −40° to about −60° C.

4. The process as claimed in claim 1, wherein the mercaptoethanol is introduced first and the diallylamide is metered thereto in the presence of said oxygen-containing gas, said oxygen-containing gas being pure oxygen or a mixture of oxygen with one or more inert gases.

5. The process as claimed in claim 1, wherein the N,N-diallylcarboxamide is reacted with mercaptoethanol in the presence of air.

6. The process as claimed in claim 1, wherein the hydrolysis of the carboxamide of the formula (2) mentioned in claim 1 is effected using the aqueous solution of an alkali metal hydroxide or alkaline earth metal hydroxide or alkali metal carbonate or alkaline earth metal carbonate.

7. The process as claimed in claim 1, wherein the hydrolysis of the carboxamide of the formula (2) mentioned in claim 1 is effected using aqueous sodium hydroxide solution or potassium hydroxide solution.

8. The process as claimed in claim 1, wherein the reaction of the N,N-diallylcarboxamide with the mercaptoethanol is carried out in toluene or ethanol as the inert organic solvent.

9. The process as claimed in claim 1, wherein, in said step c), each mol of di(3-(2-hydroxyethylthio)-1-propyl)amine is reacted with about 4.1 to about 4.5 mol of chlorine gas.

10. The process as claimed in claim 1, wherein, in said step c), the reaction of di(3-(2-hydroxyethylthio)-1-propyl)amine with chlorine gas is carried out at a temperature in the range of about 40° C. to about 80° C.

11. The process as claimed in claim 1, wherein, in said step c), the reaction of di(3-(2-hydroxyethylthio)1-propyl)amine with chlorine gas is carried out in about 3 to about 10% aqueous hydrochloric acid.

12. The process as claimed in claim 1, wherein step c) is reacting one mol of the di(3-(2-hydroxyethylthio)-1-propyl)amine thus obtained with about 4.1 to about 4.5 mol of chlorine gas and about 3 to about 10% hydrochloric acid at temperatures of about 40° C. to about 80° C. to give di(3-(2-hydroxyethylthio)-1-propyl)amine hydrochloride.

13. The process as claimed in claim 3, wherein step c) is reacting one mol of the di(3-(2-hydroxyethylthio)-1-propyl)amine thus obtained with about 4.1 to about 4.5 mol of chlorine gas and about 3 to about 10 % hydrochloric acid at temperatures of about 40° C. to about 80° C. to give di(3-(2-hydroxyethylthio)-1-propyl)amine hydrochloride.

* * * * *